United States Patent
Magin

[19]

[11] Patent Number: 6,163,722

[45] Date of Patent: Dec. 19, 2000

[54] DEFIBRILLATOR HAVING A MONITOR WITH ROTATABLE SCREEN CONTENT

[75] Inventor: Thomas Magin, Umkirch, Germany

[73] Assignee: Marquette Hellige GmbH, Freiburg, Germany

[21] Appl. No.: 09/185,454

[22] Filed: Nov. 3, 1998

[30] Foreign Application Priority Data

Nov. 14, 1997 [DE] Germany .......................... 197 50 632

[51] Int. Cl.$^7$ ...................................................... A61N 1/39
[52] U.S. Cl. .................................................................. 607/5
[58] Field of Search .................................................. 607/5

[56] References Cited

U.S. PATENT DOCUMENTS

| | | | |
|---|---|---|---|
| 4,187,858 | 2/1980 | Day et al. | 128/710 |
| 4,590,943 | 5/1986 | Paull et al. | 128/419 D |
| 5,566,098 | 10/1996 | Lucente et al. | 364/708.1 |
| 5,935,152 | 8/1999 | Merry et al. | |

FOREIGN PATENT DOCUMENTS

| | | | |
|---|---|---|---|
| 0167122 | 1/1986 | European Pat. Off. | A61N 1/39 |
| 0431581 | 6/1991 | European Pat. Off. | G09G 1/00 |
| 0609500 | 8/1994 | European Pat. Off. | G06F 15/42 |
| 0 757 912 A2 | 2/1997 | European Pat. Off. | A61N 1/39 |
| 2301201 | 11/1996 | United Kingdom | G06F 19/00 |

OTHER PUBLICATIONS

Product Brochure for CardioServ Version 4, Marquette Hellige Medical Systems, pp. 53 and 91.
Bruker Product Brochure for Defigard 1001 and 1002.
Bruker Product Brochure for Defigard 2002.
Product Brochure for CardioServ Version 3, Marquette Hellige Medical Systems, p. 6–6.

*Primary Examiner*—Carl H. Layno
*Attorney, Agent, or Firm*—Michael, Best et al.; Christian G. Cabou; Phyllis Y. Price

[57] ABSTRACT

A defibrillator (1) including an integrated surveillance monitor (10) having a screen capable of displaying vital parameters of a patient, a built-in power supply device (9) for supplying power independently of an external power supply, and a connection device (2, 3, 7) for connecting the external power supply to the defibrillator where the screen content automatically rotates on the application of the external power supply.

18 Claims, 1 Drawing Sheet

DEFIBRILLATOR HAVING A MONITOR WITH ROTATABLE SCREEN CONTENT

BACKGROUND OF THE INVENTION

The present invention relates to a defibrillator having an integrated surveillance monitor, on the screen of which vital parameters of a patient can be displayed in the form of a rotatable screen content, having a built-in power supply device for power supply independent of the main power supply and having a connection device for the external power supply of the defibrillator.

SUMMARY OF THE INVENTION

Defibrillators for external or transthoracic defibrillation form part of the equipment of rescue facilities, such as in particular rescue vehicles, and are thus used in differing practical situations, namely on the one hand directly at the place of application outside the rescue facility and on the other hand during transport of the patient using the rescue facility. That is to say that the defibrillator is removed from the rescue facility upon arrival of the rescue facility at the place of application, in order to be utilized for the treatment of the patient, who is usually lying on the ground. During transport of the patient to the hospital using the rescue facility, the defibrillator is likewise needed; however, for this purpose it is inserted into a special mounting within the rescue facility.

When used outside the rescue facility the defibrillator is powered by means of its own power supply, i.e. preferably an accumulator, while the defibrillator inserted in its mounting within the rescue facility draws its energy from the on-board power supply of the rescue facility; in this case, the accumulator of the defibrillator is at the same time recharged from the on-board power supply.

A defibrillator has a substantially parallelepipedic housing, which, in the course of treatment of a patient outside the rescue facility, rests flat on the ground. Within the rescue facility for reasons of space the defibrillator is inserted "edgewise" into its mounting.

This differing arrangement of the defibrillator in the case of use outside the rescue facility and in the case of use within the rescue facility now gives rise to a shortcoming, and the most widely varying efforts have already been made to eliminate this shortcoming.

As is known, a defibrillator does indeed have a surveillance monitor, on which the vital parameters of a patient are displayed. These vital parameters include at least an electrocardiogram (ECG) and, where appropriate, further quantities in addition. Accordingly, the surveillance monitor provides the physician or paramedic with a report on the success or lack of success of the use of the defibrillator on the patient. Thus, constant observation by the physician or paramedic is of great importance.

As has, however, already been explained hereinabove, the defibrillator is situated in different positions when used outside the rescue facility and when used within the rescue facility; this necessarily also involves different positions of the surveillance monitor, and thus of the screen thereof.

This means that an image which appears in "normal" form on the screen when the defibrillator is used outside the rescue facility appears in "vertically inverted" form in the case of use within the rescue facility when the defibrillator is situated in a mounting, since, as a consequence of the different positioning of the defibrillator, the screen has been rotated through 180°. It does not need to be emphasized that the viewing and evaluation of a "vertically inverted" image is extremely laborious for the physician or paramedic.

To overcome this problem, a defibrillator has already been developed, the screen content of which can be rotated by means of the actuation of an operating element. Thus, in addition to the operating elements which are needed for medical reasons, such defibrillators also have a further operating element which has to be actuated and set separately after the defibrillator has been inserted into the mounting within the rescue facility, in order to obtain the signal display on the screen of the surveillance monitor in the accustomed fashion, i.e. "not vertically inverted".

However, precisely when a patient is brought into a rescue facility, the most widely varying necessary actions have to be performed by the physician or paramedic, so that the setting of a separate operating element on the defibrillator to rotate the screen content thereof is perceived as troublesome.

Accordingly, it is the object of the present invention to provide a defibrillator having a surveillance monitor with a rotatable screen content, in the case of which a physician or paramedic obtains the display of the screen content in the correct arrangement and not "vertically inverted" on the surveillance monitor of the defibrillator, without additional manipulations or settings, irrespective of the place of application of the defibrillator outside or within a rescue facility.

In the case of a defibrillator of the initially mentioned type, this object is achieved according to the invention in that the screen content is automatically rotatable in dependence on the application of the external power supply.

Thus, the invention follows a surprisingly simple path: by means of a sensor, it is discerned whether the power supply of the defibrillator is being effected via the on-board power supply of the rescue facility. If it is found that the power supply is being undertaken via the on-board power supply of the rescue facility, then the screen content displayed on the surveillance monitor of the defibrillator is rotated through 180°, and vice versa. It is thus achieved that, after insertion of the defibrillator in its mounting within the rescue facility and after the establishment of contact of contact springs of the defibrillator with The on-board power supply of the rescue facility, the screen content is immediately rotated without manual intervention by the physician or paramedic, so that it can again be viewed in the normal position and not "vertically inverted". In this case no additional manipulations or settings are necessary, so that it is also the case that, for this purpose, the treatment of the patient does not need to be interrupted.

In this way, the invention permits a special advantage, namely an "automatic" rotation of the screen content on the surveillance monitor, in dependence on the place of application of the defibrillator; this was not possible previously, with the prior art.

As the defibrillator's power supply device independent of the on-board power supply use is preferably made of an accumulator which, upon application of the external power supply, can automatically be recharged from the on-board power supply of the rescue facility.

In a development of the invention, it is provided that the rotatability of the screen content can be activated in dependence on the power supply prior to the first inception of operation of the defibrillator. That is to say that it is possible that the rotatability of the screen content is not activated. This may be expedient in special cases, in which, on an exceptional basis, the defibrillator is accommodated within the rescue facility in such a way that its surveillance monitor is in the same position as outside the rescue facility. In this case, a rotatability of the screen content is undesired, so that the activation of the rotatability is expediently not undertaken.

In this connection, it should be mentioned that rescue facilities are to be understood in general as referring to motor vehicles, rail vehicles, aeroplanes, helicopters and watercraft, although, of course, motor vehicles represent quite preferred areas of application. Where sufficient space is available, the defibrillator is not necessarily inserted "edgewise" in a mounting within the rescue facility; this means that, as has been explained hereinabove, the surveillance monitor reproduces its screen content in the normal position.

Another development of the present invention resides in that the screen content can additionally be rotated by means of a manually actuated switch. On this basis, it is achieved that in exceptional cases the rotation of the screen content can be undertaken manually, i.e. as in the case of the abovementioned, already existing systems; this is advisable, for example, in circumstances in which the defibrillator cannot be powered, in the rescue facility, from the on-board power supply of the latter, because, for example, that power supply has interruptions to the contact springs.

Finally, another development of the invention resides in a microcontroller, connected downstream of the connection devices, for the surveillance of the voltage present at the connection devices. Such a microcontroller is particularly advantageous for the detection of the voltage delivered by the on-board power supply of the rescue facility.

DETAILED DESCRIPTION OF THE PREFERRED EMBODIMENT

Figure 1:
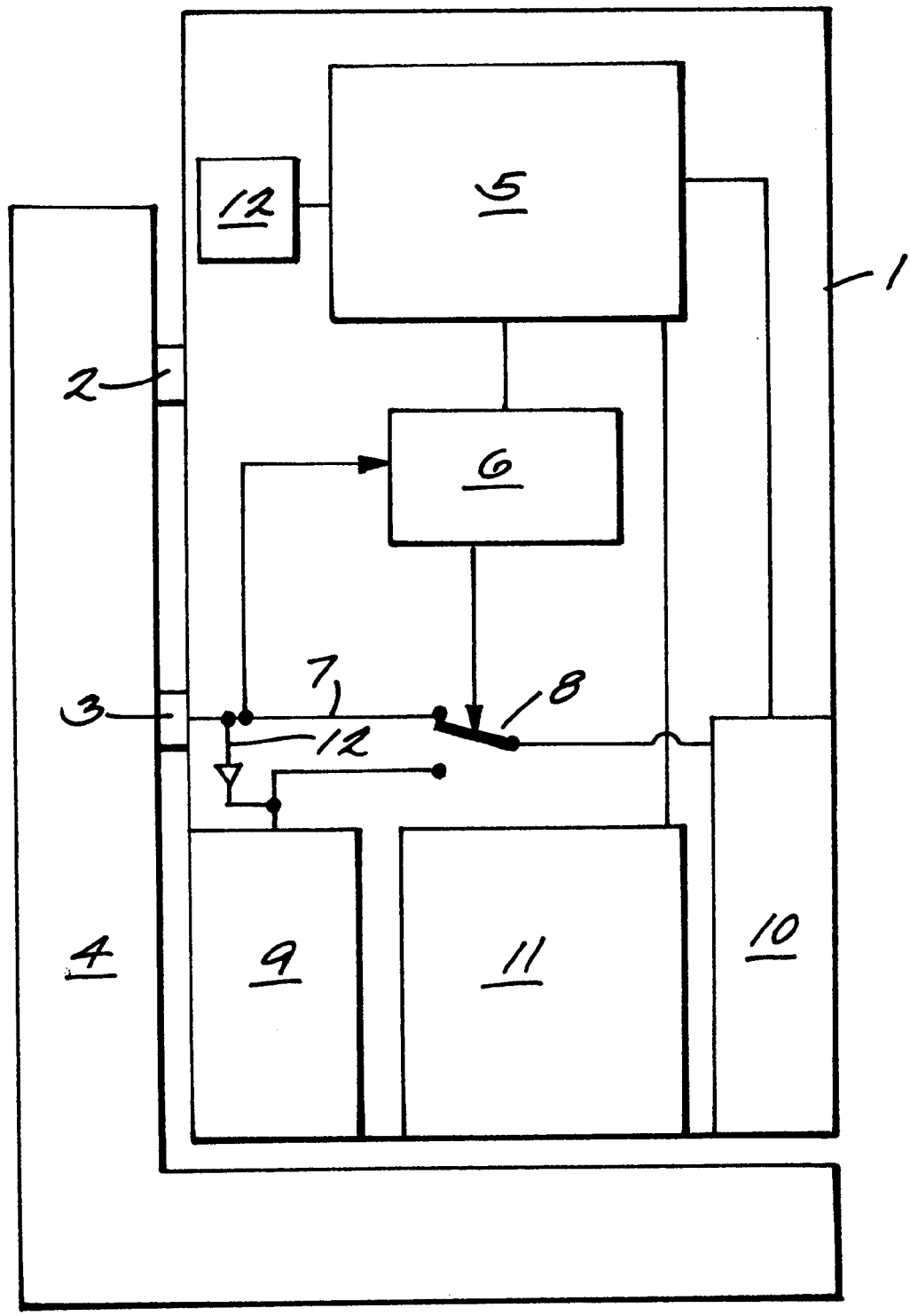
FIG. 1 is a block diagrams representing a defibrillator embodying the invention.

In the text which follows, the invention is explained in greater detail with reference to the single drawing in which a block diagram of the defibrillator according to the invention is diagrammatically represented.

The FIGURE shows a defibrillator 1, which is attached by means of contact springs 2, 3 to a mounting 4 of a rescue facility which is not shown. Earth potential is for example supplied via the contact spring 2, while the on-board power supply having the supply of 12V is applied to the contact spring 3.

In the defibrillator 1 there are a main microprocessor 5 for controlling the defibrillator in its, entirety, and a microcontroller 6 which scans an input line 7 connected to the contact spring 3 in the case of insertion into the mounting 4 and controls a switch 8 in dependence on the detected voltage. This switch 8 is connected either to the input line 7 for supply via the on-board power supply or to an accumulator 9. In place of the accumulator, it is also possible to use, for example, a battery.

It should be noted that this accumulator 9 is recharged when the defibrillator 1 is connected to the on-board power supply; this is diagrammatically indicated in the FIGURE by a corresponding line 12 with diode.

In addition, the defibrillator 1 includes a surveillance monitor 10 having a screen, for example a liquid crystal display, as well as a high voltage section 11. The high voltage section 11 delivers—controlled by the main microprocessor 5—current pulses having a time duration of approximately 4–8 ms for electrodes of the size of the palm of the hand which are to be applied to the chest wall of the patient (not shown). As has already been explained hereinabove, the vital parameters of the patient are displayed on the screen of the surveillance monitor 10.

When the defibrillator 1 has been taken out of the mounting 4, the microcontroller 6 then detects that a power supply via the input line 7 is no longer present. It then switches over the switch 8 to the accumulator 9, so that the latter powers the main microprocessor 5, the surveillance monitor 10 and the high voltage section 11.

When the defibrillator 1 has been taken out of the mounting 4, it is then laid flat on the ground, in order to be in a stable position for a treatment of a patient. In this position, the surveillance monitor 10 displays the screen content in the correct position for a physician or paramedic on its screen.

When, following a first emergency treatment, the patient is then brought together with the defibrillator into the rescue facility and the defibrillator is inserted into the mounting 4, the screen content then appears on the surveillance monitor 10 in a form which is per se "vertically inverted". Since, however, the microcontroller 10 immediately detects that, following contacting via the contact springs 2, 3, the power supply is being effected from the on-board power supply of the rescue facility, since 12V are present at the input line 7, it immediately switches over the switch 8 to the on-board power supply, so that the latter now powers the defibrillator 1. Simultaneously with this switching over, a rotation of the screen content on the screen of the surveillance monitor 10 through 180° is effected by means of the microprocessor 5, so that the screen content can now be normally read, within the rescue facility as well, from the point of view of the physician or paramedic.

The defibrillator 1 is designed in such a way that the rotatability of the screen content can be activated via the main microprocessor 5 in dependence on the power supply via input line 7 or the on-board power supply, prior to the first inception of operation of the defibrillator 1. Practical applications are indeed feasible in which such an activation is not desired, when for example the defibrillator is likewise anchored in a "flat position" within the rescue facility. Accordingly, the rotatability of the screen content does not necessarily need to be activated.

Moreover, it is also possible to provide an additional manual switch (likewise not shown) by means of which the rotation of the screen content can be undertaken manually, independently of the power supply.

What is claimed is:

1. A defibrillator comprising an integrated surveillance monitor (10) having a screen capable of displaying vital parameters of a patient in the form of a rotatable screen content, a built-in power supply device (9) for supplying power independently of an external power supply, and a connection device (2, 3, 7) for connecting the external power supply to the defibrillator, wherein the screen content automatically rotates on the application of the external power supply.

2. A defibrillator according to claim 1, wherein the built-in power supply (9) is an accumulator which is rechargeable upon application of the external power supply.

3. A defibrillator according to claim 1, wherein the automatic rotatability of the screen content is activated in dependence on the application of the external power supply prior to a first inception of operation of the defibrillator (1).

4. A defibrillator according to claim 1, further comprising a switch capable of manually rotating the screen content independent of the external power supply.

5. A defibrillator according to claim 1, further comprising a microcontroller (6) connected downstream of the connection device (2, 3, 7) for the surveillance of a voltage present at the connection device (2, 3, 7).

6. A defibrillator, comprising:
- an integrated surveillance monitor (10) having a screen capable of displaying vital parameters of a patient in the form of a rotatable screen content;
- a built-in power supply device (9) for supplying power independently of an external power supply and being rechargeable upon application of the external power supply; and
- a connection device (2, 3, 7) for connecting the external power supply to the defibrillator, wherein the screen content automatically rotates on the application of the external power supply prior to a first inception of operation of the defibrillator (1).

7. A defibrillator according to claim 6, further comprising:
- a switch capable of manually rotating the screen content independent of the external power supply.

8. A defibrillator according to claim 7, further comprising a microcontroller (6) connected downstream of the connection device (2, 3, 7) for surveillance of a voltage present at the connection device.

9. A method of displaying a screen content on a defibrillator, the defibrillator comprising a screen capable of displaying the screen content and a connection device for connecting an external power supply to the defibrillator, the method comprising the acts of:
- displaying the screen content on the screen with a first orientation when the external power supply is applied to the connection device; and
- displaying the screen content on the screen with a second orientation when the external power supply is removed from the connection device.

10. A method according to claim 9, further comprising the act of:
- powering the defibrillator with the external power supply when the external power supply is applied to the connection device.

11. A method according to claim 9, wherein the defibrillator further comprises a built-in power supply, the method further comprising the act of:
- powering the defibrillator with the built-in power supply when the external power supply is removed from the connection device.

12. A method according to claim 10, wherein the defibrillator further comprises a built-in power supply, the method further comprising the act of:
- charging the built-in power supply when the external power supply is applied to the connection device.

13. A method according to claim 9, wherein the defibrillator further comprises a microcontroller, the method further comprising the act of:
- monitoring the connection device with the microcontroller to determine if a voltage is present.

14. A method of displaying a screen content on a defibrillator, the defibrillator comprising a screen capable of displaying the screen content, a connection device for connecting an external power supply to the defibrillator, and a manual switch capable of being placed in a first and second position, the method comprising the acts of:
- placing the manual switch in a first position;
- displaying the screen content on the screen with a first orientation when the external power supply is applied to the connection device and when the manual switch is in the first position;
- displaying the screen content on the screen with a second orientation when the external power supply is removed from the connection device and the manual switch is in the first position;
- placing the manual switch in a second position; and
- manually controlling the orientation of the screen content when the manual switch is in the second position.

15. A method according to claim 14, further comprising the act of:
- powering the defibrillator with the external power supply when the external power supply is applied to the connection device.

16. A method according to claim 14, wherein the defibrillator further comprises a built-in power supply, the method further comprising the act of:
- powering the defibrillator with the built-in power supply when the external power supply is removed from the connection device.

17. A method according to claim 15, wherein the defibrillator further comprises a built-in power supply, the method further comprising the act of:
- charging the built-in power supply when the external power supply is applied to the connection device.

18. A method according to claim 14, wherein the defibrillator further comprises a microcontroller, the method further comprising the act of:
- monitoring the connection device with the microcontroller to determine if a voltage is present.

* * * * *